United States Patent
Kim

(10) Patent No.: US 10,561,705 B2
(45) Date of Patent: Feb. 18, 2020

(54) AGONIST PEPTIDE FOR ADIPONECTIN RECEPTOR

(71) Applicant: Brian Byeoung Kim, Yongin-si (KR)

(72) Inventor: Brian Byeoung Kim, Yongin-si (KR)

( * ) Notice: Subject to any disclaimer, the term of this patent is extended or adjusted under 35 U.S.C. 154(b) by 0 days.

(21) Appl. No.: 15/776,407

(22) PCT Filed: Apr. 10, 2017

(86) PCT No.: PCT/KR2017/003872
§ 371 (c)(1),
(2) Date: May 15, 2018

(87) PCT Pub. No.: WO2018/056541
PCT Pub. Date: Mar. 29, 2018

(65) Prior Publication Data
US 2018/0325981 A1  Nov. 15, 2018

(30) Foreign Application Priority Data

Sep. 20, 2016 (KR) .......... 10-2016-0119821
Mar. 24, 2017 (KR) .......... 10-2017-0037762

(51) Int. Cl.
| | | |
|---|---|---|
| *C07K 7/08* | (2006.01) | |
| *C07K 7/00* | (2006.01) | |
| *A61K 38/06* | (2006.01) | |
| *A61K 38/00* | (2006.01) | |
| *A61P 3/10* | (2006.01) | |
| *A61K 38/10* | (2006.01) | |

(52) U.S. Cl.
CPC ............. *A61K 38/10* (2013.01); *A61P 3/10* (2018.01); *C07K 7/08* (2013.01)

(58) Field of Classification Search
CPC .......... A61K 38/10; A61K 38/00; C07K 7/08; C07K 7/00; C07K 14/5759; A61P 3/10
USPC ....... 514/6.8, 6.9, 21.5, 21.4, 21.3; 530/300, 530/326, 325, 324
See application file for complete search history.

(56) References Cited

U.S. PATENT DOCUMENTS

| | | | | |
|---|---|---|---|---|
| 7,592,423 | B2 * | 9/2009 | Zalevsky ........... | C07K 14/5759 530/350 |
| 9,073,965 | B2 | 7/2015 | Otvos et al. | |
| 2013/0273567 | A1 | 10/2013 | Kadowaki et al. | |
| 2016/0222077 | A1 | 8/2016 | Hahn et al. | |

FOREIGN PATENT DOCUMENTS

KR    10-2015-0032401 A    3/2015

OTHER PUBLICATIONS

International Search Report for PCT/KR2017/003872 dated Jul. 10, 2017 from Korean Intellectual Property Office.
Otvos et al., "Design and development of a peptide-based adiponectin receptor agonist for cancer treatment", BMC, Biotechnology, vol. 11, Article No. 90 (internal pp. 1-14) 2011.
Sun et al., "Identification of Adiponectin Receptor Agonist Utilizing a Fluorescence Polarization Based High Throughput Assay", Plos One, vol. 8, Issue 5, Article No. e63354 (internal pp. 1-8) (2013).
Okada-Iwabu et al., "A small-molecule AdipoR agonist for type 2 diabetes and short life in obesity", Nature, vol. 503, pp. 493-499 (2013).

* cited by examiner

*Primary Examiner* — Julie Ha
(74) *Attorney, Agent, or Firm* — Sughrue Mion, PLLC

(57) ABSTRACT

A peptide comprising SEQ ID NO: 1 (Xaa1-Tyr-Phe-Ala-Tyr-His-Pro-Asn-Ile-Pro-Gly-Leu-Xaa2-Tyr-Phe), wherein Xaa1 is any one selected from the group consisting of tyrosine, tryptophan, phenylalanine and non-natural amino acids having characteristics identical to tyrosine, tryptophan or phenylalanine; and Xaa2 is any one selected from the group consisting of tyrosine, tryptophan, phenylalanine, and non-natural amino acids having the characteristics identical to tyrosine, tryptophan or phenylanine is described.

9 Claims, 6 Drawing Sheets
Specification includes a Sequence Listing.

FIG. 1

| Code | Sequence (SEQ ID NO) | Concept | Kd (uM) |
|---|---|---|---|
| 3-1 | YYFAYHPNIPGLYYF (SEQ ID NO: 1 where Xaa1 and Xaa13 each is tyrosine) | Shorten (15mer) | 16 |
| 3-3 | NIPGLWYFAY (SEQ ID NO: 5) | Y6 replacement | 30.7 |
| 3-4 | NIPGLFYFAY (SEQ ID NO: 6) | Y6 replacement | 23.2 |
| 4-3 | WYFAYHPNIPGLWYF (SEQ ID NO: 1 where Xaa1 and Xaa13 each is tryptophan) | 15mer | 6-10 |
| 4-4 | FYFAYHPNIPGLFYF (SEQ ID NO: 1 where Xaa1 and Xaa13 each is phenylalanine) | 15mer | 2-4.3 |
| 4-5 | YSFAYHPNIPGLYYF (SEQ ID NO: 7) | Solubility | 24.5 |

AGONIST PEPTIDE FOR ADIPONECTIN RECEPTOR

BACKGROUND OF THE INVENTION

Field of the Invention

The present invention relates generally to the fields of pharmacy, cell biology, and molecular biology, more particularly to an agonist peptide that acts on the adiponectin receptor for the treatment of type 2 diabetes.

Description of the Related Art

Diabetes is a serious metabolic disease with hyperglycemia. It is caused by defects in insulin secretion or abnormal function of insulin, such as insulin secretion reduction, resistance to insulin, etc., due to genetic or environmental factors, as a result of which glucose in blood is not transferred to or stored in cells and remains in an excessively large amount in blood, resulting in hyperglycemia, in which the blood glucose level is much higher than that of normal people. Diabetes is largely classified into type 1 diabetes (T1), type 2 diabetes and gestational diabetes.

In particular, type 2 diabetes, to which the present invention relates, accounts for most of the diabetes occurring in the Republic of Korea. Unlike type 1 diabetes, which occurs mostly in children, type 2 diabetes occurs mainly in adults. It occurs because of an insufficient amount of insulin secretion in vivo or resistance to insulin due to cells which do not respond to insulin.

Diabetes symptoms can be controlled through weight loss, healthy diet, sufficient exercise, and continuous monitoring of blood sugar level. However, although this disease can be controlled in the early stages with drugs, it gradually worsens and eventually requires insulin injections due to its progressive nature. Overweight and obese people are known to have a much higher risk of developing type 2 diabetes than normal weight people because they secrete chemicals that can destabilize the cardiovascular/metabolic system. It can be said that the risk of developing type 2 diabetes increases with age, but this can be considered to a result of an increase in body weight and a decrease in physical exercise.

The existing antidiabetics are largely classified into insulin preparations, sulphonylurea-based drugs, thiazolidinedione (TZD)-based drugs, biguanide-based drugs, α-glucosidase inhibitors, meglitinide-based drugs, incretin mimetics, DPP-IV inhibitors, etc. If, after diagnosis of diabetes, dietary and exercise therapies fail, the diabetes is usually treated with a single or combination therapy of antidiabetics, with reference to the guidelines of the American Diabetes Association (ADA). Here, the primary drug is metformin, which is a biguanide-based drug, and the secondary and tertiary drugs are sulfonylurea-based drugs, glinide-based drugs, thiazolidinedione-based drugs, DPP4 inhibitors, etc. Thereafter, GLP-1 (glucagon like peptide-1) agonist injections or insulin injections are used.

Phenformin and metformin, which belong to biguanides, have been used as antidiabetics since 1957. However, since phenformin produced side effects of lactic acidosis, it has been banned in many countries. Currently, metformin is the most commonly used type 2 antidiabetic in the world. Metformin lowers the blood sugar level without causing hypoglycemia or facilitating insulin secretion. Further, metformin does not influence, or slightly reduces, body weight and has beneficial effects on plasma lipids. The major side effect of metformin therapy occurs in digestive organs. Patients taking 2,550 mg of metformin per day experience abdominal discomfort, abdominal inflation, metallic taste, etc.

TZD-based drugs derived from clofibrate, which is a hyperlipidemia treatment with some hypoglycemic effect, are antidiabetics which have a hypoglycemic effect and some hyperlipidemia treatment effect. TZDs reduce resistance to insulin and boost insulin-induced blood sugar consumption, as well as control the blood sugar level by increasing the glucose consumption rate in muscle and fat and suppressing blood sugar production in the liver. TZDs are a ligand of PPARγ, a gene that generally regulates genes involved in lipocyte differentiation and lipoprotein metabolism. Activation of PPARγ by TZDs results in lipocyte differentiation, improved glucose consumption in lipocytes and improved resistance to insulin. It is known that since PPARγ is expressed in a very small amount in muscle cells and is not expressed in hepatocytes, the improved resistance to insulin by TZD in muscle is due to an indirect effect resulting from its action in lipocytes. The main side effects of TZD-based drugs are weight gain, edema, etc.

α-Glucosidase inhibitors (AGIs) are drugs that are not absorbed. They are not drugs that improve the pathological defects of type 2 diabetes. α-Glucosidase is an enzyme present in the brush border of the small intestine. It breaks down carbohydrates such as starch, dextrin, and maltose into absorbable monosaccharides. Inhibitors of the enzyme do not prevent but delay the absorption of digested carbohydrates, inhibiting the sharp increase of postprandial blood sugar and insulin concentrations. In type 2 diabetic patients, adequate amounts of insulin are not secreted or insulin is secreted slowly, in response to the elevated blood sugar level following ingestion of food. Delay of the absorption of glucose in the small intestine allows the pancreas to secrete adequate amounts of insulin, thus preventing a rapid rise in postprandial blood sugar level. The rapid rise in postprandial blood sugar level is closely related to cardiovascular mortality rate. Side effects of AGIs mostly occur in the digestive system, which include abdominal pain, farts, and diarrhea. These side effects result from fluid retraction caused by an osmotic pressure generated when unabsorbed carbohydrates pass through the large intestine. The farts result from the gaseous products produced by the metabolism of carbohydrates by GI flora.

The existing oral antidiabetics currently used in clinical practice cause various side effects such as hypoglycemia, diarrhea, abdominal inflation, weight gain, lactic acidosis, cardiotoxicity and hepatotoxicity on long-term use, as well as the positive effects of sustained normalization of blood sugar. Moreover, these drugs irreversibly damage/destroy the beta cells of the pancreas, which secrete insulin, and cause resistance to insulin, leading to reduced efficacy, and eventually the patient requires insulin injections. In addition, insulin, which is the most commonly used antidiabetic, causes patient inconvenience/intolerance because it needs to be subcutaneously injected 2-3 times per day, and also has a great possibility of causing hypoglycemia. Therefore, it is necessary to develop a more effective and safe drug that can effectively reduce the blood sugar level without causing hypoglycemia as well as overcome the weight gain and resistance to insulin while protecting the pancreatic beta cells even on long-term use. Also, it is urgently required to develop a long-lasting antidiabetic for the patient's convenience.

SUMMARY OF THE INVENTION

Technical Problem

The purpose of the present invention is to provide an agonist peptide designed based on adiponectin receptor analysis and thereby to provide an antidiabetic which is more effective than the conventional medicines in a wide variety of treatment such as alleviation of insulin resistance while minimizing the side effects of antidiabetics, especially type 2 antidiabetics.

It is to be understood that the technical problem to be solved by the present invention is not limited to the foregoing problems. Other technical problems not mentioned herein will be apparent to a person skilled in the art from the following description.

Solution to Problem

In order to achieve the above objective, a peptide according to one aspect of the present invention may comprise:

```
                                        SEQ ID NO: 1
(Xaa1-Tyr-Phe-Ala-Tyr-His-Pro-Asn-Ile-Pro-Gly-Leu-
Xaa2-Tyr-Phe),
``` wherein Xaa1 is any one selected from the group consisting of tyrosine, tryptophan, phenylalanine and non-natural amino acids having characteristics identical to tyrosine, tryptophan or phenylalanine; and Xaa2 is any one selected from the group consisting of tyrosine, tryptophan, phenylalanine, and non-natural amino acids having the characteristics identical to tyrosine, tryptophan or phenylalanine.

In the peptide, an amino acid sequence of X-L1 may be further linked to the N-terminal of the amino acid sequence, wherein X is any one selected from the group consisting of:

1 to 10 amino acids, linear or branched polyethylene glycols with a weight of 1 to 200 kDa, lipophilic compounds, peptide transduction domains, and L1 is a compound serving as a single bond or a linker linking the N-terminal of SEQ ID NO: 1 to X.

The peptide may further comprise an amino acid sequence of L2-Z at the C-terminal of the amino acid sequence, wherein Z is any one selected from the group consisting of:

1 to 10 amino acids;

linear or branched polyethylene glycols with a weight of 1 to 200 kDa;

lipophilic compounds; and peptide transduction domains, and

L2 is a compound serving as a single bond or a linker linking the C-terminal of SEQ ID NO: 1 to Z.

The peptide may be an agonist of the adiponectin receptor.

Dissociation constant of the peptide with the adiponectin receptor 1 may be 2 to 16 µM.

The amount of the peptide required for phosphorylation of AMP-activated protein kinase (AMPK) may be 0.8 to 4 µM.

The peptide may be any one selected from the group consisting of:

```
                                        (SEQ ID NO: 2)
Tyr-Tyr-Phe-Ala-Tyr-His-Pro-Asn-Ile-Pro-Gly-Leu-
Tyr-Tyr-Phe;

(SEQ ID NO: 3)
Trp-Tyr-Phe-Ala-Tyr-His-Pro-Asn-Ile-Pro-Gly-Leu-
Trp-Tyr-Phe;
and (SEQ ID NO: 4)
Phe-Tyr-Phe-Ala-Tyr-His-Pro-Asn-Ile-Pro-Gly-Leu-
Phe-Tyr-Phe.
```

A composition according to another aspect of the present invention may comprise a polynucleotide encoding the peptide.

A pharmaceutical composition for therapeutic use according to another aspect of the present invention may be a composition for the prevention or treatment of type 2 diabetes comprising the peptide as an active component.

Effects of the Invention

According to one embodiment of the present invention, the agonist peptide for the adiponectin receptor has a better affinity for ADIPOR1 than the reference peptide ADP355. According to another embodiment of the present invention, the agonist peptide for the adiponectin receptor can facilitate AMPK phosphorylation more effectively than the reference peptide ADP355.

It is to be understood that the effects of the present invention are not limited to the foregoing effects, but include all effects that can be deduced from the constitution of the invention described in the detailed description or the claims of the present invention.

BRIEF DESCRIPTION OF THE DRAWINGS

FIG. 1 shows the dissociation constant values of synthetic peptides (3 peptides from 3rd round, 4 peptides from 4th round) from the adiponectin receptor ADIPOR1, measured by surface plasmon resonance experiments.

THE BEST MODE FOR IMPLEMENTING THE PRESENT INVENTION

Figure 2:
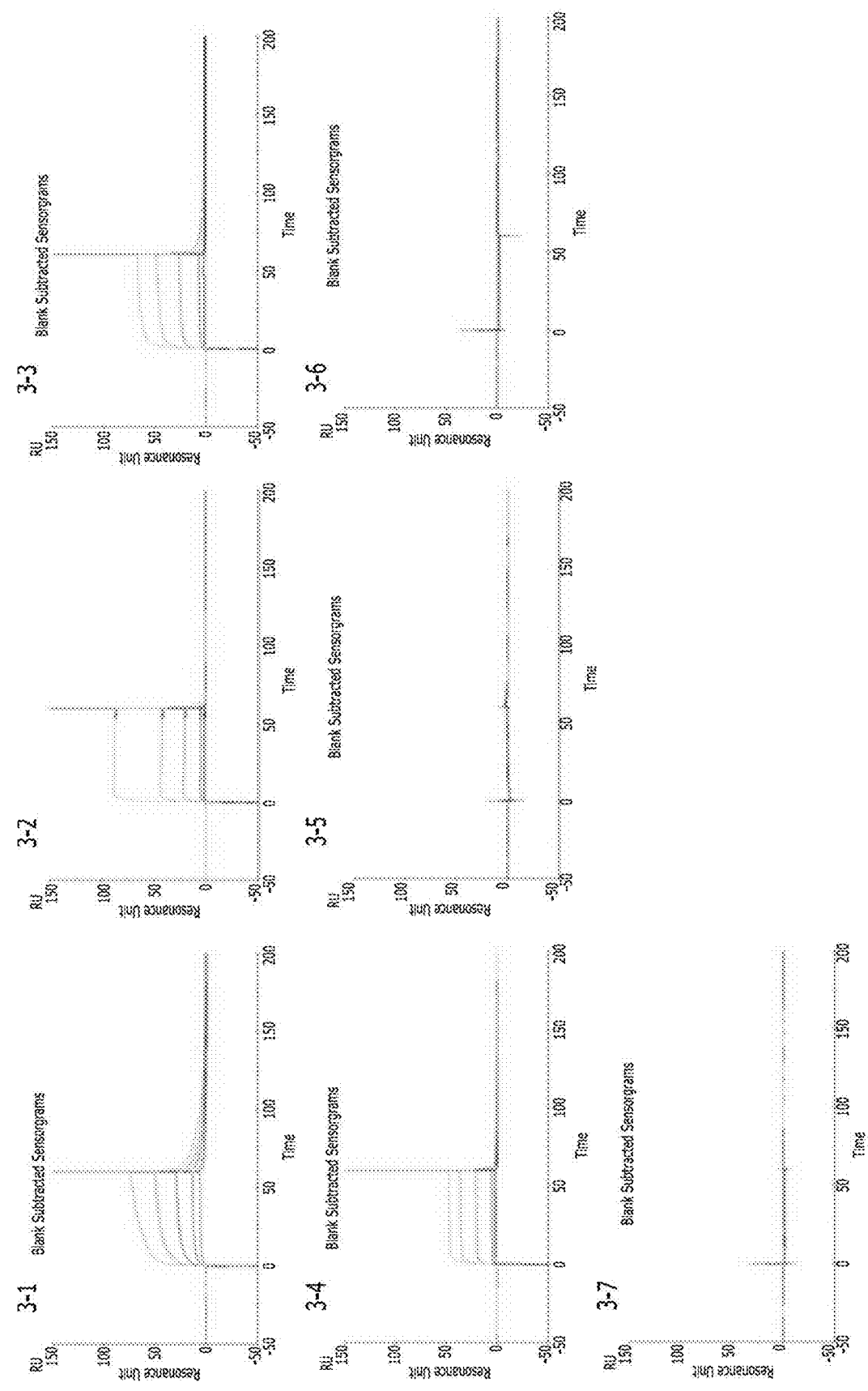
FIG. 2 shows a graph indicating the dissociation constant values of 3rd round peptides, measured by surface plasmon resonance experiments.

Hereinafter, examples of the present invention will be described in detail so that a person skilled in the art can easily carry out the present invention. The present invention may, however, be embodied in many different forms and should not be construed as limited to the examples described herein.

Example 1: Synthesis, Isolation and Purification of ADIPOR1 Recombinant Protein The ADIPOR1 protein sequence used was the same as that used for the ADIPOR1 structure analysis, in which 88 amino acids at the N-terminal have been removed. The gene capable of producing the protein sequence was synthesized by codon optimization (IDT). At the time, a BamHI restriction enzyme site, a Flag tag and a TEV protease recognition sequence (ENLYFQG; SEQ ID NO: 11) were inserted at the 5' end and an EcoRI restriction enzyme site was inserted at the 3' end in order to facilitate cloning and purify the expressed protein. The obtained gene was inserted into the pFASTbac1 vector required for baculovirus production to perform cloning. The cloned vector was transfected into DH10 bac (Invitrogen) to obtain a bacmid comprising the ADIPOR1 gene through recombination. In order to produce baculovirus, the obtained bacmid was transfected into SF9 cells ($5 \times 10^4$ cells) using Transfectine (Qiagen), and the baculovirus secreted in a medium was collected after 5 days. Then, a large amount of baculovirus was produced through amplification. The obtained baculovirus was inoculated into SF9 cells ($5 \times 10^6$ cells/ml) cultured in a 1 L SFM900 medium, and protein was expressed at a temperature of 27° C. for 3 days. The SF9 cells expressing recombinant ADIPOR1 were obtained through centrifugation. The obtained cell pellets were aliquoted and stored at −80° C., and used in protein purification as needed to minimize the disadvantages of membrane proteins, which have the possibility of inactivation due to storage after purification. The ADIPOR1, which is a membrane protein expressed on a cell membrane, was solubilized using a detergent (1% DDM) for purification. The dissolved sample was reacted with anti-Flag antibody bead (Sigma) for 1 hour in ice. Then, ADIPOR1 bound to the anti-Flag antibody bead was eluted with Flag peptide. The primarily purified ADIPOR1 was subjected to size exclusion chromatography (Supderdex200, GE healthcare) to obtain only monomeric, proteins. In the purification using size exclusion chromatography, 0.1% DDM, 0.005% CHS, 20 mM HEPES, and 150 mM NaCl buffer were used.

Example 2: Maintenance of Cells

C2C12 and HepG2 cells were purchased from ATCC. Before use, they were cultured in a DMEM (Hyclone) medium supplemented with 10% FBS (Hyclone) and 1% penicillin/streptomycin in an incubator at 37° C. in a 5% $CO_2$ environment.

Example 3: C2C12 Myotube Differentiation

C2C12 cells were plated in 12 wells. When they showed a confluency of 80% or more, they were washed once with PBS. Then, the medium was replaced with a differentiation medium in which DMEM is supplemented with 2.5% horse serum and 1% penicillin/streptomycin. Thereafter, differentiation was performed for 5-7 days, replacing the medium with a new differentiation medium every day. The thus-obtained product was used for experiments.

Example 4: Treatment, Sampling and Immunoblotting of Compounds

It has already been reported that adiponectin or adiporon was most effective when applied to differentiated C2C12 for 5-15 minutes, and that when ADP355 was applied for 15, 30, 45, 60 minutes after 1-hour recovery following 24-hour starvation in various cancer cell lines, it was the most effective at 30 minutes. Based on the prior finding, after optimization of the number of the cells to be used for experiment, HepG2 was starved for 5 hours, recovered, and treated with peptide for 30 minutes, and C2C12 was starved for 24 hours and treated with peptide for 10 minutes. The treated cell samples were washed once with cold PBS and lysed for 15 minutes with a RiPA buffer containing a protease inhibitor and a phosphatase inhibitor. After 15 minutes, centrifugation was carried out at 14000 rpm for 5 minutes to collect only proteins. After quantification, 4× sample buffer and 2-ME were added to prepare a sample for western blotting. The western blotting was performed using a conventional western blotting technique. The antibodies of AMPK, p-AMPK, p-AKT, p-ACC and GAPDH were diluted to 1:1000 or 1:2000 depending on the type thereof and imaging was performed with a LAS-4000 instrument.

Test Example 1: Observation of the Bound Peptide and Measurement of the Binding Force Using Surface Plasmon Resonance (SPR)

In order to analyze the binding force between peptide and ADIPOR1, a purified recombinant ADIPOR1 (A88) was bound to a CM5 chip with 3000 RU or higher through amine coupling. Peptide was diluted with a running buffer (0.1% DDM, 0.005% CHS, 10 mM HEPES, 150 mM NaCl with pH 7.4) and injected into a SPR instrument at various concentrations to analyze the binding force. The affinity value was calculated using the affinity fitting or kinetics fitting method. In order to analyze peptide solubility, peptide stocks were prepared with DMSO, diluted in an appropriate buffer, and then undissolved precipitates were removed. The peptide concentrations were calculated by measuring the extrusion coefficient and A280 absorbance of each peptide.

The affinity of the peptides synthesized in a total of four rounds was identified. In particular, the affinities of 3rd round and 4th round peptides are shown in FIGS. 2 and 3, respectively.

The detailed explanation of FIG. 2 is as follows:
Peptide 3-1: cyan: 100 uM, pink: 25 uM, blue: 10 uM, green: 5 uM, orange: 2.5 uM
Other peptides: yellow: 50 uM: 25 uM, pink: 10 uM, blue: 2.5 uM, green: 1 uM, red: 0.5 uM
Peptide 3-1 of FIG. 2 shows a Kd value of up to 16 uM, which is higher than other designed peptides, and thus it has a relatively high affinity.

Figure 3:
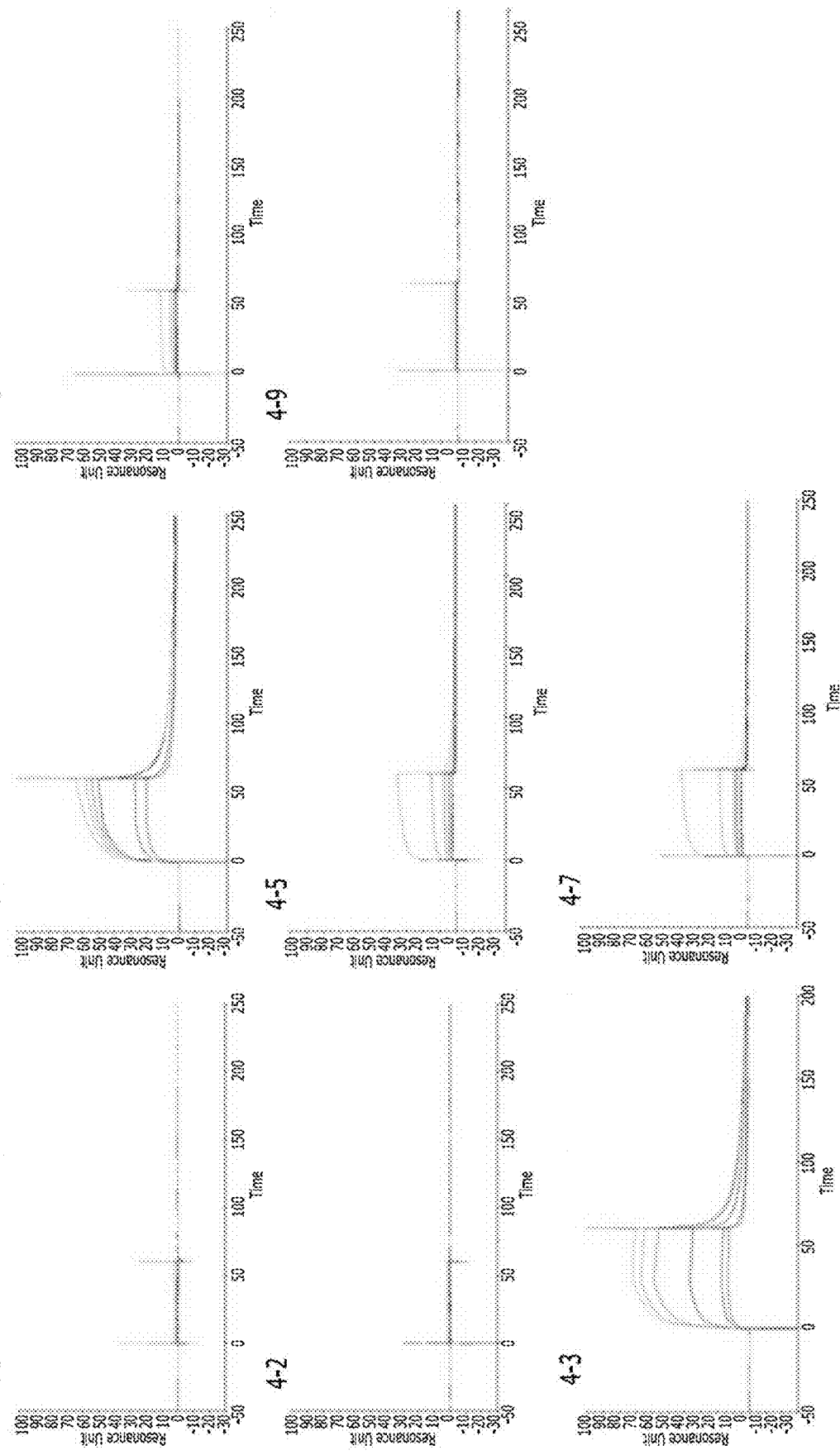
FIG. 3 shows a graph indicating the dissociation constant values of 4th round peptides, measured by surface plasmon resonance experiments.

The detailed explanation of FIG. 3 is as follows:
Yellow: 50 uM, cyan: 25 uM, pink: 12.5 uM, blue: 6.25 uM, green: 3.12 uM, orange: 1.56 uM
In FIG. 3, peptides 4-3 and 4-4 show the measured Kd values of 6-10 uM and 2-4.3 uM, respectively.

Test Example 2: Assessment of Drug Efficacy in HepG2 Cell Line

HepG2 cell line was plated on a 12-well plate at a concentration of $8*10^5$ cells/well on the day before the experiment. After overnight cultivation, they were starved in a serum free medium for 5 hours, and then treated for 30 minutes with reference peptide ADP355, peptide 3-1, peptide 4-3 and peptide 4-4 with concentrations of 20 uM, 4 uM and 0.8 uM, in addition to DMSO 0.4% (MOCK) and 10 ug/ml of adiponectin. Then, they were lysed with a RIPA buffer. Samples were prepared and boiled for 10 min at 95° C. Then, 12 ug thereof was loaded to perform western blotting.

Figure 4:
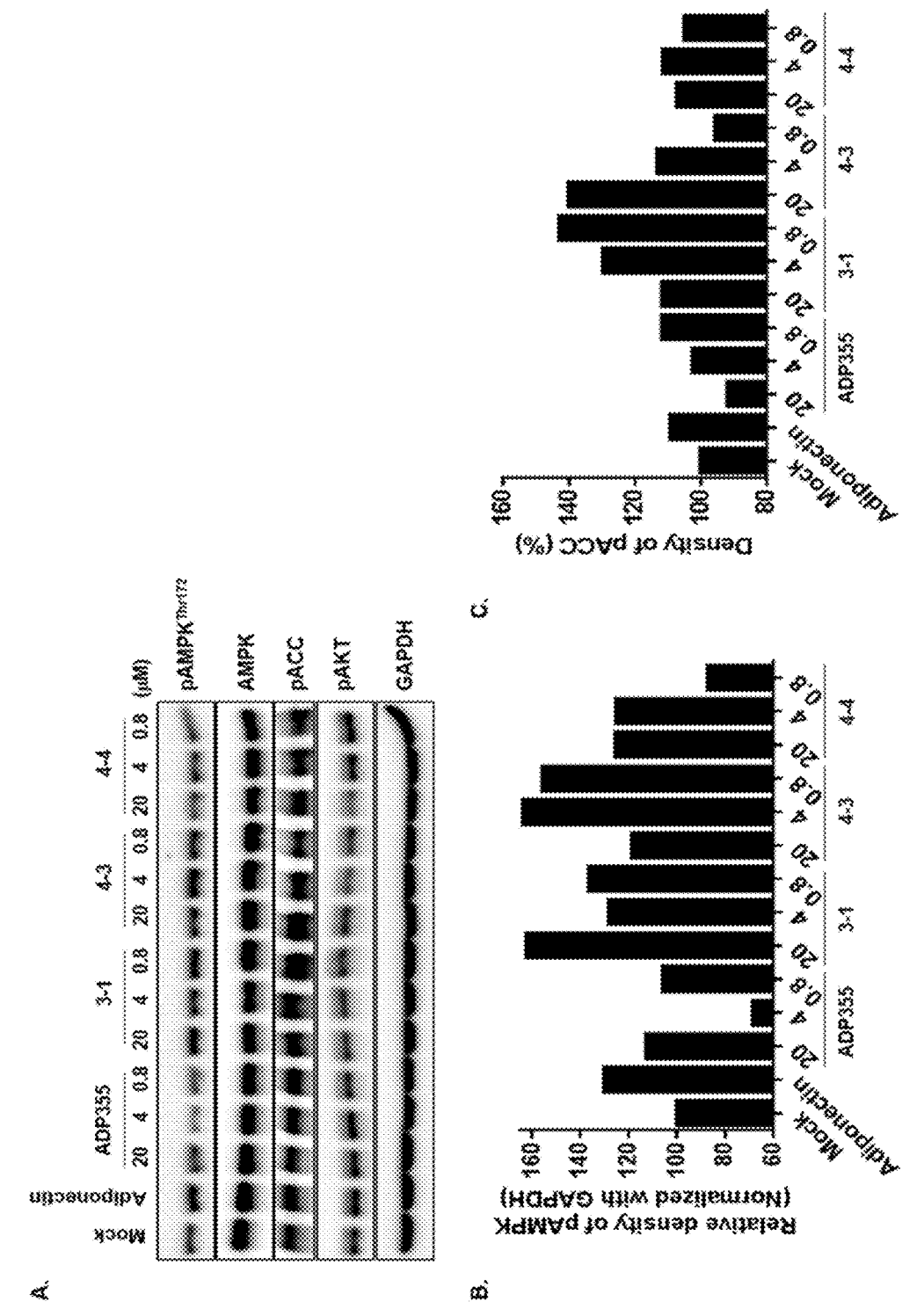
FIG. 4 shows the results of western blotting in the HepG2 cell line for measurement of AMPK phosphorylation activity of peptide 3-1, peptide 4-3 and peptide 4-4.

FIG. 4 shows the western blotting results, and the detailed description thereof is as follows:

A. Western blotting results according to the concentration of reference peptide ADP355, peptide 3-1, peptide 4-3, and peptide 4-4

B. Relative density of pAMPK of reference peptide ADP355, peptide 3-1, peptide 4-3, and peptide 4-4

C. Relative density of pACC of reference peptide ADP355, peptide 3-1, peptide 4-3, and peptide 4-4

FIG. 4 shows the AMPK phosphorylation activity of reference peptide ADP355, peptide 3-1, peptide 4-3, and peptide 4-4 in the HepG2 cell line.

Test Example 3: C2C12 Myotube Differentiation and Assessment of Efficacy in C2C12 Cell Line C2C12 cells were plated on a 12-well plate. When they showed a confluency of 80% or more, they were washed once with PBS. Then, the medium was replaced with a differentiation medium in which DMEM is supplemented with 2.5% horse serum and 1% penicillin/streptomycin. Thereafter, differentiation was performed for 5-7 days, replacing the medium with a new differentiation medium every day. The thus-obtained cells were used for the test.

$8*10^5$ C2C12 cell lines were plated on a 12-well plate, and differentiated to myotubes according to the above method. Then, they were treated for 10 minutes with reference peptide ADP355, peptide 3-1, peptide 4-3 and peptide 4-4 with concentrations of 20 uM, 4 uM and 0.8 uM, in addition to DMSO 0.4% (MOCK) and 10 ug of adiponectin. Then, western blotting was performed according to the same method for the HepG2 cell line.

Figure 5:
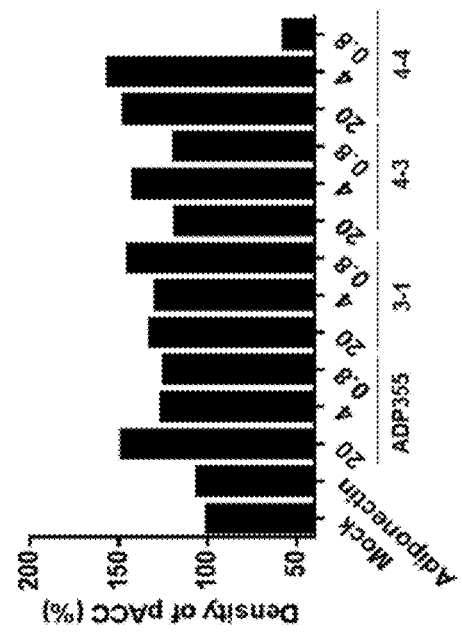
FIG. 5 shows the results of western blotting in the C2C12 cell line for measurement of AMPK phosphorylation activity of peptide 3-1, peptide 4-3 and peptide 4-4.
Figure 5:
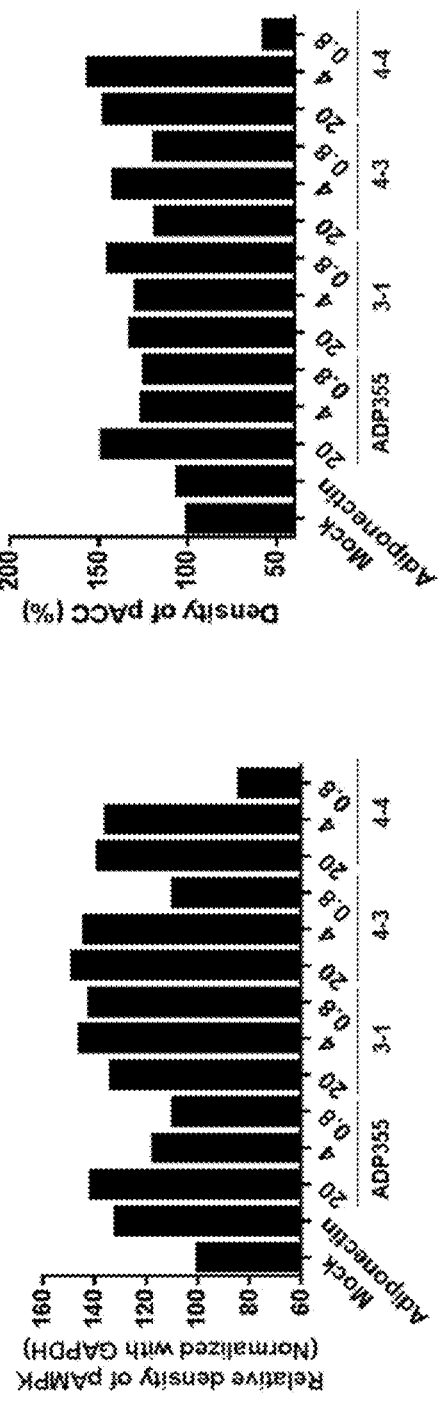
Figure 5:
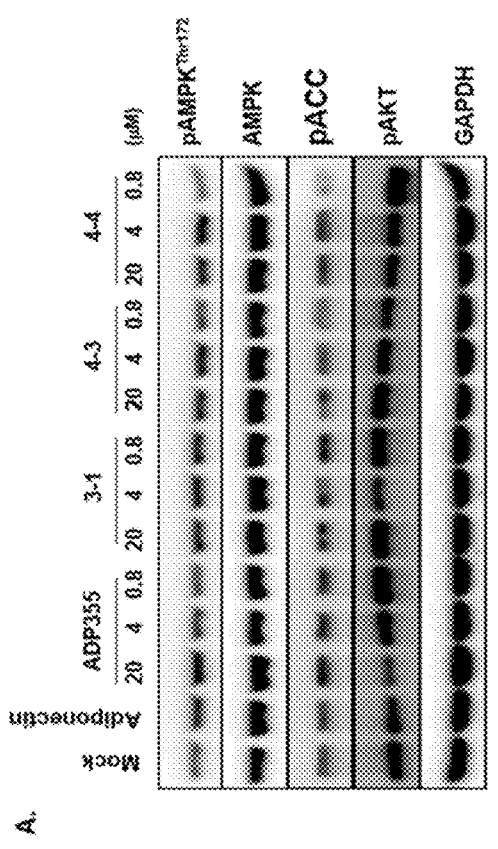

FIG. 5 shows the western blotting results, and the detailed description thereof is as follows:

A. Western blotting results according to the concentration of reference peptide ADP355, peptide 3-1, peptide 4-3, and peptide 4-4

B. Relative density of pAMPK of reference peptide ADP355, peptide 3-1, peptide 4-3, and peptide 4-4

C. Relative density of pACC of reference peptide ADP355, peptide 3-1, peptide 4-3, and peptide 4-4

FIG. 5 shows the AMPK phosphorylation activity of reference peptide ADP355, peptide 3-1, peptide 4-3, and peptide 4-4 in the C2C12 cell line.

It will be understood that the foregoing descriptions of the present invention are for illustrative purposes. A person skilled in the art will readily understand that the embodiments can be modified into other specific forms without departing from the spirit or essential characteristics of the present invention. It is therefore to be understood that the above-described embodiments are illustrative in all aspects and not restrictive. For example, each of the elements which are described as a single entity may be implemented separately, and likewise, the elements which are described as separate entities may be implemented in a combined form.

The scope of the present invention is defined by the appended claims, and all changes or modifications derived from the meaning and scope of the claims and their equivalents should be construed as being included within the scope of the present invention.

DETAILED DESCRIPTION OF THE EMBODIMENTS

Hereinafter, the present invention will be described with reference to the accompanying drawings. The present invention may, however, be embodied in many different forms and should not be construed as limited to the embodiments set forth herein. In order to clearly illustrate the present invention, parts not related to the description are omitted, and similar parts are denoted by similar reference numerals throughout the specification.

As used herein, the phrase that a part is "linked (bound, bonded)" with another part covers not only the case of "directly linked" but also the case of "indirectly linked" via a member located therebetween. Also, the phrase that a part "comprises (includes)" an element means that it does not exclude, and may further include, another element, unless specifically stated otherwise.

The terminology used herein is only for the purpose of describing particular embodiments and is not intended to limit the invention. The singular forms include plural referents unless the context clearly dictates otherwise. It is to be understood that, as used herein, the terms "comprise", "include", and "have" indicate the presence of stated features, numbers, steps, actions, elements, components, or combinations thereof but do not preclude the presence or addition of one or more other features, numbers, steps, actions, elements, components, or combinations thereof.

Hereinafter, embodiments of the present invention will be described in detail with reference to the accompanying drawings.

The adiponectin, which is a polypeptide derived from lipocytes, binds to an adiponectin receptor ADIPOR1 or 2 to participate in AMPK or PPAR-a signaling. Obese people are known to have a low blood adiponectin level, and it is known that the low blood adiponectin level increases resistance to insulin and thus causes type 2 diabetes. A protein that is secreted in the adipose tissue and exerts activity in other organs is called adipokine or adipocytokine. Adiponectin is a type of adipokine. Adiponectin has an inherent characteristic that when its secretion is reduced, fat accumulation increases. Further, adiponectin increases insulin sensitivity by reducing blood fatty acid concentration and triglyceride levels in the liver and muscle, reduces TNF-a-induced mononuclear cell adhesion to vascular endothelial cells, and produces anti-inflammatory and antiatherogenic effects by suppressing platelets. Also, it facilitates phosphorylation of acetyl-CoA carboxylase (ACC), fatty acid consumption, glucose intake, and lactate production in muscle. In the liver, it decreases the molecules involved in ACC phosphorylation and gluconeogenesis, thereby lowering the blood sugar level.

Adiponectin is present and circulates in the blood in the form of trimer or hexamer. In particular, the globular domain of adiponectin is known to have a binding site for ADIPOR1. The major binding fragment thereof is known to be amino acids 153 to 162 (Asn-Ile-Pro-Gly-Leu-Tyr-Tyr-Phe-Ala-Tyr; SEQ ID NO: 10; adiponectin active region).

The adiponectin receptors include the following two receptors: ADIPOR1 and ADIPOR2, which are major receptors to which adiponectin binds. They are known to be receptor proteins with 7-transmembrane domains. In particular, ADIPOR1 is known to activate AMPK signaling. According to one embodiment of the present invention, the adiponectin receptor may be ADIPOR1 and ADIPOR2, preferably ADIPOR1.

The agonist refers to a substance or drug which binds to a receptor of a bioactive substance and performs the same (or similar) action as that of the substance or a molecule which enhances the activity of the receptor site. It includes endogenous agonists, which are produced in vivo, and exogenous agonists, which are administered. Partial agonists do not exhibit 100% pharmacological action even after bound to a receptor. Even if the dose is increased, their effects do not increase.

The peptide refers to a molecule in which two or more amino acids form a covalent bond as a peptide bond. According to one embodiment of the present invention, the peptide may be a natural peptide, a recombinant peptide or a synthetic peptide.

The amino acid refers to a molecule having a specific structure in which an amine group (—NH2) having basic properties and a carboxyl group (—COOH) having acidic properties coexist. It is an element of protein. When an amino group bonded to one amino acid molecule reacts with a carboxyl group bonded to another amino acid molecule, water and a new molecule composed of two amino acids are formed. The new molecule is called a dipeptide, and the resulting bond is called a peptide bond. The part with an amine group is called N-terminal, and the part with a carboxyl group is called C-terminal. In order to form one protein, a number of peptide bonds must be formed. There are 20 amino acids in nature. 12 of them are synthesized in our bodies from food. These are glycine, alanine, arginine, asparagine, aspartate, cysteine, glutamate, glutamine, histidine, proline, serine and tyrosine. The other 8 are isoleucine, leucine, lysine, tryptophan, valine, methionine, phenylalanine and threonine, which are not synthesized.

The non-natural amino acid refers to an amino acid that does not exist in nature, and which is synthesized or made by humans. Specific examples thereof include iodinated tyrosine, methylated tyrosine, glycosylated serine, glycosylated threonine, azetidine-2-carboxylic acid, 3,4-dehydroproline, perthiaproline, canavanine, ethionine, norleucine, selenomethionine, animohexanoic acid, telluromethionine, homoallylglycine and homopropargylglycine. D-amino acid is also included in the non-natural amino acid.

The non-natural amino acids having the identical characteristics refers to non-natural amino acids which have physically, chemically, or functionally similar characteristics as natural amino acids and which exert the same or similar effects to a natural amino acid when it replaces the natural amino acid. According to one embodiment of the present invention, the same characteristics as tyrosine, tryptophan and phenylalanine may be aromatic characteristics. The aromatic amino acid refers to an amino acid having an aromatic ring (benzene ring or its derivative) in the side chain of the amino acid. Thus, the non-natural amino acids having the same characteristics may be non-natural amino acids having the same or similar characteristics as aromatic amino acids.

The polyethylene glycol (PEG) refers to a polymer of ethylene oxide. According to one embodiment of the present invention, the polyethylene glycol may be methoxyl PEG maleimide (mPEG (MAL)), methoxyl PEG forked maleimide (mPEG2 (MAL)), methoxyl PEG ortho-pyridyldisulfide (mPEG-OPSS), PEG-vinylsulphone, or a composition of methoxyl PEG aldehyde (mPEG-ALD) and ortho-pyridyldisulfide-PEG-hydrazide (OPSS-PEG-hydrazide). According to another embodiment of the present invention, the polyethylene glycol may be selected from the group consisting of 5k-mPEG (MAL), 20k-mPEG (MAL), 40k-mPEG2(MAL), 5k-mPEG-OPSS, 10k-mPEG-OPSS, 20k-mPEG-OPSS, or a composition of mPEG30 kD-ALD and OPSS-PEG2k-hydrazide.

The lipophilic compound is a compound that exists in nature. Specifically, it may be a saturated or unsaturated fatty acid, a fatty acid diketone, a terpene, a prostaglandin, a vitamin, a carotenoid, a steroid, or a synthetic compound, specifically a carbonic acid, an alcohol, an amine or a sulfonic acid having one or more alkyl, aryl, alkenyl, or other unsaturated compounds.

The peptide transduction domain refers to a protein capable of penetrating a cell membrane protein. When it binds to another compound to form a complex, it enables the complex to enter a cell membrane. According to one embodiment of the present invention, the peptide transduction domain may be a known protein having membrane permeability characteristics.

The compound serves as a single bond or a linker, that is, the L1 or L2 are compounds located between X or Z and the N- or C-terminal of the amino acid sequence of the agonist peptide to enhance the stability of the agonist peptide. Specifically, it may be at least two functional groups. Preferably, L1 or L2 may be two or multiple functional groups, such as alkyl, aryl, aralkyl or peptide functional group.

It is apparent to a person skilled in the art that when X is not included in the agonist peptide, L1 is not included therein.

Also, it is apparent to a person skilled in the art that when Z is not included in the agonist peptide, L2 is not included therein.

According to one embodiment of the present invention, the agonist peptide for the adiponectin receptor can be designed by constructing a binding model predicted by a molecular modeling technique based on the X-ray structure analysis result of the adiponectin receptor. Here, the molecular modeling technique refers to a method of obtaining the three-dimensional structure of various molecules by using an empirical force field known as molecular mechanics, calculating therefrom the physical and chemical properties of the molecules, and visualizing them using computer graphics. The technique is to obtain a three-dimensional molecular structure closest to the actual structure of the molecule. According to the technique, the optimal structure is obtained through various possible methods (quantum mechanical calculation or X-ray database search, etc.) and the physical and chemical properties of interest are calculated by using the structure, allowing the design of new molecules based on the caculations. The software for molecular modeling includes Discovery Studio 4.1 (Biovia) and Maestro (Schrodinger).

Figure 6:
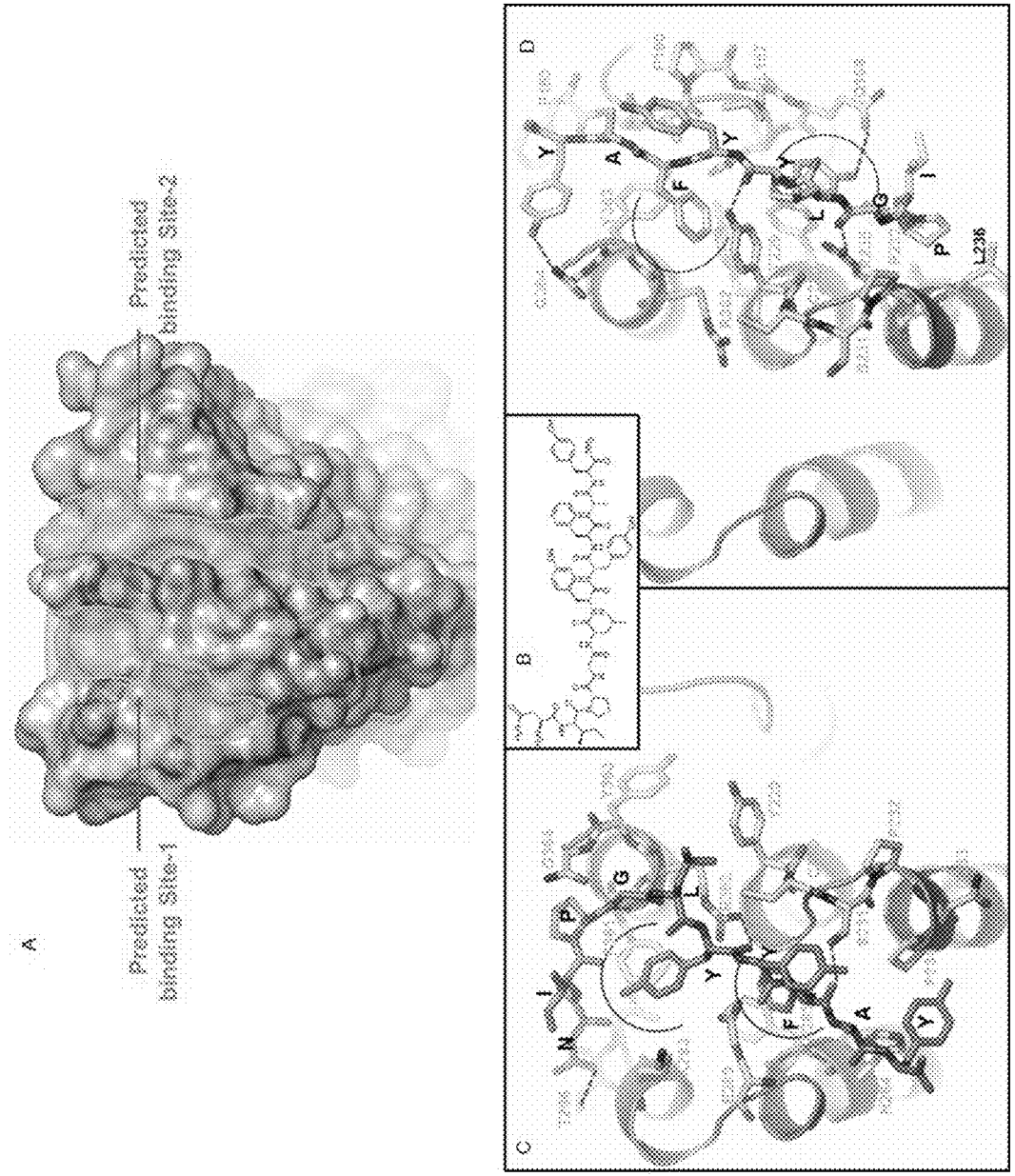
FIG. 6 shows the predicted binding sites and binding model of adiponectin, using a molecular modeling technique based on the X-ray structure analysis result of ADIPOR1 disclosed by Hiroaki Tanabe, etc.

Specifically, it is possible to construct a binding model by removing from the X-ray structure of ADIPOR1 the amino acids after residue 364 of ADIPOR1, which have a high flexibility and does not greatly affect the binding of adiponectin and the activation resulting therefrom (see FIG. 6). In the constructed binding model, Tyr158 and Phe160 of adiponectin may bind to a hydrophobic pocket of ADIPOR1. Here, a hydrophobic pocket is one of the sites where a ligand protein binds to a adiponectin receptor, and a site where the amino acid of a ligand is capable of hydrophobic binding to a adiponectin receptor.

With reference to FIG. 6, FIG. 6-A shows the adiponectin binding pockets. The binding model of adiponectin active region (see FIG. 6-B) with each pocket may be constructed as shown in FIGS. 6-C and 6-D. As can be seen from the binding model for predicted binding-site (FIG. 6-C), tyrosine (Y) and phenylalanine (F) moieties of adiponectin may enter a hydrophobic pocket (blue pocket). The hydrogen bond between each amide bond backbone and ADIPOR1 is represented by a red dotted line. Similarly, in the binding model for predicted binding-2 site, it was confirmed that tyrosine (Y) and phenylalanine (F) moieties may enter a hydrophobic pocket and form an additional hydrogen bond.

Agonist peptides for the adiponectin receptor may be designed based on the constructed binding models. Also, known agonist peptides for the adiponectin receptor may be used. According to one embodiment of the present invention, the active region of adiponectin, which is an agonist peptide of ADIPOR1, ADP355(H-DAsn-Ile-Pro-Nva-Leu-Tyr-DSer-Phe-Ala-DSer-NH2; SEQ ID NO: 8), and ADP399(H-DAsn-Ile-Pro-Nva-Leu-Tyr-DSer-Phe-Ala-DSer-His-Pro)2-Dab-NH2; SEQ ID NO: 9) may be used.

The dissociation constant refers to an equilibrium constant when the law of mass action is valid between molecules not dissociated and atoms or atom groups generated by dissociation. The dissociation constant is used to measure the binding force or affinity between the receptor and each ligand. The dissociation constant may be used to determine the affinity between the agonist peptide for the adiponectin receptor of the present invention and the adiponectin receptor.

With reference to FIGS. 3 and 4, surface plasmon resonance (SPR) experiments were performed in the present invention to measure the dissociation constant between the agonist peptide and the adiponectin receptor, particularly adiponectin receptor 1 (ADIPOR1). First, an expressed and purified adiponectin receptor ADIPOR1 was immobilized and its dissociation constant from candidate peptides was measured over a total of 4 rounds. FIG. 3 shows the results of the measurement of dissociation constants of 3rd round peptide candidates. In particular, peptide 3-1, which has the amino acid sequence of SEQ ID NO: 2, had a dissociation constant value of 16 uM or less, which shows a better affinity than the reference peptide ADP355, which was developed by Laszlo Otvos, et al. and is known to be another agonist of ADIPOR1 and which has a dissociation constant value of 100 uM or more. FIG. 4 shows the measurement results of the affinity of peptide candidates in 4th round. Peptide 4-3, which has the amino acid sequence of SEQ ID NO: 3, and peptide 4-4, which has the amino acid sequence of SEQ ID NO: 4, respectively exhibited dissociation constant values of 6-10 uM and 2-4.3 uM, which also indicates a better affinity than the dissociation constant value of the reference peptide ADP355 of 100 uM or more.

AMP-activated protein kinase (AMPK), which is a serine/threonine kinase, is known to be a regulator of lipid and glucose metabolism and plays an important regulatory role in diabetes and obesity. AMPK is activated by AMP, which is increased upon intracellular energy consumption, and inhibits ATP use. It plays a key role in inducing catabolism and thereby maintaining energy homeostasis. In terms of lipid metabolism, AMPK activation inhibits fatty acid synthase (FAS) and acetyl CoA carboxylase (ACC), which are enzymes inducing fatty acid synthesis, and suppresses HMG-CoA reductase, a rate-limiting enzyme for cholesterol biosynthesis, thus affecting the regulation of in vivo lipid production. In the process of glucose production, it inhibits gluconeogenesis. It also increases the amount of GLUT4 in muscle cells to increase glucose transport to the muscle. Therefore, induction of AMPK activation in diabetic patients has various therapeutic mechanisms.

FIG. 4 shows the results of western blotting to measure the phosphorylation of AMPK. Here, the western blotting was performed on peptide 3-1 with the amino acid sequence of SEQ ID NO: 2, peptide 4-3 with the amino acid sequence of SEQ ID NO: 3 and peptide 4-4 with the amino acid sequence of SEQ ID NO: 4 in the HepG2 cell line, which is a hepatocyte cell line. The western blotting results showed that peptide 3-1 and peptide 4-3 phosphorylated AMPK from its lowest concentration of 0.8 uM, indicating that they have a much higher efficacy than ADP355, which was found to cause a slight phosphorylation at 20 uM. Further, when examining the effects of the above three peptides on the phosphorylation of ACC, a downstream protein of AMPK, it was observed that peptides 3-1 and 4-3 phosphorylated ACC to the same or more extent than the reference peptide ADP-355 (see FIGS. 4-A and 4-C).

FIG. 5 shows the results of western blotting to measure the phosphorylation of AMPK. Here, the western blotting was performed on peptide 3-1, peptide 4-3 and peptide 4-4 in the C2C12 cell line. The results showed that peptide 3-1 phosphorylated AMPK even at a low concentration of 0.8 uM, but that peptide 4-3, peptide4-4, and the reference peptide ADP355 caused phosphorylation from 4 uM. From these results, it was confirmed that peptide 3-1 has the most excellent activity (see FIGS. 5-A and 5-B). Also, it was confirmed that phosphorylation of ACC, a downstream protein of AMPK, was increased under all the conditions except for 0.8 uM of peptide 4-4 (see FIGS. 5-A and 5-C).

The polynucleotide according to another aspect of the present invention refers to a product obtained when a nucleotide is linked to another nucleotide by a covalent bond between a phosphoric acid and a sugar to form a chain. Examples thereof include DNA and RNA. A nucleotide is a unit constituting a nucleic acid and consists of a phosphoric acid, a sugar, and a base. The basic unit of DNA is called a deoxyribonucleotide, and the unit of RNA is called a ribonucleotide. The sugar of nucleotide is a monosaccharide composed of 5 carbons. When the second carbon atom has a hydroxyl group, it is called a ribose. When the carbon atom has only hydrogen without oxygen, it is called a deoxyribose. Ribose constitutes RNA and deoxyribose constitutes DNA. The bases constituting DNA are adenine (A), guanine (G), cytosine (C), and thymine (T). In RNA, uracil (U) is used instead of thymine as its base.

The pharmaceutical composition according to yet another aspect of the present invention may comprise an agonist peptide for the adiponectin receptor as an active ingredient. It is obvious that various pharmaceutically acceptable carriers or other additives may be added to the pharmaceutical composition, in addition to the agonist peptide for the adiponectin receptor, and thus the detailed description thereof will be omitted.

What is claimed is:

1. A peptide comprising SEQ ID NO: 1(Xaa1-Tyr-Phe-Ala-Tyr-His-Pro-Asn-Ile-Pro-Gly-Leu-Xaa2-Tyr-Phe),
    wherein Xaa1 is any one selected from the group consisting of tyrosine and tryptophan, phenylalanine and non-natural amino acids having compatible characteristics as aromatic amino acids; and
    Xaa2 is any one selected from the group consisting of tyrosine, tryptophan, phenylanine, and non-natural amino acids having compatible characteristics as aromatic amino acids.

2. The peptide according to claim 1,
    wherein X-L1 is further linked to the N-terminal of the peptide sequence,
    wherein X is any one selected from the group consisting of:
    linear or branched polyethylene glycols with a weight of 1 to 200 kDa,
    lipophilic compounds, and
    peptide transduction domains, and
    wherein L1 is a compound serving as a single bond or a linker linking the N-terminal of SEQ ID NO: 1 to X.

3. The peptide according to claim 1,
    wherein L2-Z at the C-terminal of the peptide sequence,
    wherein Z is any one selected from the group consisting of:
    linear or branched polyethylene glycols with a weight of 1 to 200 kDa,
    lipophilic compounds, and
    peptide transduction domains, and
    wherein L2 is a compound serving as a single bond or a linker linking the C-terminal of SEQ ID NO: 1 to z.

4. The peptide according to claim 1, the peptide is an agonist of the adiponectin receptor.

5. The peptide according to claim 1, wherein dissociation constant of the peptide with the adiponectin receptor 1 is 2 to 16 µM.

6. The peptide according to claim 1,
    wherein the peptide phosphorylates AMP-activated protein kinase (AMPK), and
    wherein the amount of the peptide required for phosphorylating AMP-activated protein kinase (AMPK) is 0.8 to 4 µM.

7. The peptide according to claim 1,
    wherein SEQ ID NO: 1 is any one selected from the group consisting of:

```
                                          (SEQ ID NO: 2)
Tyr-Tyr-Phe-Ala-Tyr-His-Pro-Asn-Ile-Pro-Gly-Leu-
Tyr-Tyr-Phe;

(SEQ ID NO: 3)
Trp-Tyr-Phe-Ala-Tyr-His-Pro-Asn-Ile-Pro-Gly-Leu-
Trp-Tyr-Phe;
and
                                          (SEQ ID NO: 4)
Phe-Tyr-Phe-Ala-Tyr-His-Pro-Asn-Ile-Pro-Gly-Leu-
Phe-Tyr-Phe.
```

8. A pharmaceutical composition for treating type 2 diabetes, comprising the peptide of claim 1 as an active component.

9. A method for treating type 2 diabetes comprising administering the peptide of claim 1 as an active component to a subject in need thereof.

* * * * *

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: AGONIST PEPTIDE FOR ADIPONECTIN RECEPTOR
```

```
<220> FEATURE:
<221> NAME/KEY: MUTAGEN
<222> LOCATION: (1)..(15)
<223> OTHER INFORMATION: Xaa1 is any one selected from the group
      consisting of tyrosine, tryptophan and phenylalanine ; Xaa13 is
      any one selected from the group consisting of tyrosine, tryptophan
      and phenylalanine

<400> SEQUENCE: 1

Xaa Tyr Phe Ala Tyr His Pro Asn Ile Pro Gly Leu Xaa Tyr Phe
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: AGONIST PEPTIDE FOR ADIPONECTIN RECEPTOR

<400> SEQUENCE: 2

Tyr Tyr Phe Ala Tyr His Pro Asn Ile Pro Gly Leu Tyr Tyr Phe
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: AGONIST PEPTIDE FOR ADIPONECTIN RECEPTOR

<400> SEQUENCE: 3

Trp Tyr Phe Ala Tyr His Pro Asn Ile Pro Gly Leu Trp Tyr Phe
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: AGONIST PEPTIDE FOR ADIPONECTIN RECEPTOR

<400> SEQUENCE: 4

Phe Tyr Phe Ala Tyr His Pro Asn Ile Pro Gly Leu Phe Tyr Phe
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: AGONIST PEPTIDE FOR ADIPONECTIN RECEPTOR(3-3)

<400> SEQUENCE: 5

Asn Ile Pro Gly Leu Trp Tyr Phe Ala Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: AGONIST PEPTIDE FOR ADIPONECTIN RECEPTOR(3-4)

<400> SEQUENCE: 6

Asn Ile Pro Gly Leu Phe Tyr Phe Ala Tyr
1               5                   10
```

```
<210> SEQ ID NO 7
<211> LENGTH: 15
<212> TYPE: PRT
<213> ORGANISM: Artificial Sequence
<220> FEATURE:
<223> OTHER INFORMATION: AGONIST PEPTIDE FOR ADIPONECTIN RECEPTOR(4-5)

<400> SEQUENCE: 7

Tyr Ser Phe Ala Tyr His Pro Asn Ile Pro Gly Leu Tyr Tyr Phe
1               5                   10                  15

<210> SEQ ID NO 8
<211> LENGTH: 10
<212> TYPE: PRT
<213> ORGANISM: Artificial Sequence
<220> FEATURE:
<221> NAME/KEY: MUTAGEN
<222> LOCATION: (1)..(10)
<223> OTHER INFORMATION: ADP355; Xaa1 at position1 is D-Asn, Xaa4 is
      Nva, Xaa7 is D-Ser, Xaa10 is D-Ser

<400> SEQUENCE: 8

Xaa Ile Pro Xaa Leu Tyr Xaa Phe Ala Xaa
1               5                   10

<210> SEQ ID NO 9
<211> LENGTH: 25
<212> TYPE: PRT
<213> ORGANISM: Artificial Sequence
<220> FEATURE:
<221> NAME/KEY: MUTAGEN
<222> LOCATION: (1)..(25)
<223> OTHER INFORMATION: ADP399; Xaa1 and Xaa13 each is D-Asn, Xaa4 and
      Xaa16 each is Nva, Xaa7 and Xaa19 each is D-Ser, Xaa10 and Xaa20
      each is D-Ser, Xaa26 is Dab

<400> SEQUENCE: 9

Xaa Ile Pro Xaa Leu Tyr Xaa Phe Ala Xaa His Pro Xaa Ile Pro Xaa
1               5                   10                  15

Leu Tyr Xaa Phe Ala Xaa His Pro Xaa
            20                  25

<210> SEQ ID NO 10
<211> LENGTH: 10
<212> TYPE: PRT
<213> ORGANISM: Artificial Sequence
<220> FEATURE:
<223> OTHER INFORMATION: Adiponectin active region

<400> SEQUENCE: 10

Asn Ile Pro Gly Leu Tyr Tyr Phe Ala Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: TEV protease recognition site

<400> SEQUENCE: 11

Glu Asn Leu Tyr Phe Gln Gly
1               5
```